United States Patent
Han et al.

(10) Patent No.: US 10,019,789 B2
(45) Date of Patent: Jul. 10, 2018

(54) QUALITY ASSURANCE SYSTEM FOR RADIATION THERAPY EQUIPMENT, AND QUALITY ASSURANCE METHOD THEREOF

(71) Applicant: Samsung Life Public Welfare Foundation, Seoul (KR)

(72) Inventors: Youngyih Han, Seoul (KR); Eun Hyuk Shin, Seoul (KR); Jung Suk Shin, Seoul (KR); Hee Chul Park, Seoul (KR); Doo Ho Choi, Seoul (KR); Jun Sang Cho, Seoul (KR)

(73) Assignee: Samsung Life Public Welfare Foundation, Seoul (KR)

( * ) Notice: Subject to any disclaimer, the term of this patent is extended or adjusted under 35 U.S.C. 154(b) by 0 days.

(21) Appl. No.: 14/779,668

(22) PCT Filed: Oct. 24, 2014

(86) PCT No.: PCT/KR2014/010083
§ 371 (c)(1),
(2) Date: Sep. 24, 2015

(87) PCT Pub. No.: WO2015/060691
PCT Pub. Date: Apr. 30, 2015

(65) Prior Publication Data
US 2016/0225132 A1 Aug. 4, 2016

(30) Foreign Application Priority Data

Oct. 24, 2013 (KR) .................. 10-2013-0127240

(51) Int. Cl.
*G06K 9/00* (2006.01)
*G06T 7/00* (2017.01)
*A61N 5/10* (2006.01)

(52) U.S. Cl.
CPC .......... *G06T 7/0004* (2013.01); *A61N 5/1075* (2013.01); *G06T 7/0002* (2013.01);
(Continued)

(58) Field of Classification Search
None
See application file for complete search history.

(56) References Cited

U.S. PATENT DOCUMENTS

2002/0181660 A1* 12/2002 Reinstein ............. A61N 5/1048
378/205
2004/0184583 A1 9/2004 Nagamine et al.
2015/0036806 A1* 2/2015 Wong .................. A61N 5/1075
378/207

FOREIGN PATENT DOCUMENTS

JP 2003-299639 A 10/2003
JP 2003-532934 A 11/2003
(Continued)

OTHER PUBLICATIONS

International Search Report, issued by KIPO, acting as the International Searching Authority, for international application PCT/KR2014/010083 dated Nov. 27, 2014 with English translation.
(Continued)

*Primary Examiner* — Atiba O Fitzpatrick
(74) *Attorney, Agent, or Firm* — McCarter & English, LLP

(57) ABSTRACT

A quality assurance system for radiation therapy equipment includes an image capturing unit installed on radiation therapy equipment and capturing an image of an indicating part indicating an operational state of the radiation therapy equipment, an image processing unit extracting an edge of the indicating part in image captured by the image capturing unit, a center point extraction unit extracting a center point with respect to the edge, and a quality evaluation unit
(Continued)

evaluating quality of the radiation therapy equipment by tracking movement of the center point.

7 Claims, 14 Drawing Sheets

(52) U.S. Cl.
CPC .... *A61N 5/1081* (2013.01); *A61N 2005/1059* (2013.01); *G06T 2207/10116* (2013.01); *G06T 2207/30168* (2013.01)

(56) References Cited

FOREIGN PATENT DOCUMENTS

| | | |
|---|---|---|
| JP | 2008-131981 A | 6/2006 |
| JP | 2008-283531 A | 11/2008 |
| JP | 2009-039411 A | 2/2009 |
| JP | 2013-022309 A | 2/2013 |
| KR | 10-2007-0054630 A | 5/2007 |
| KR | 10-2009-0093654 A | 9/2009 |
| WO | WO 99/09887 A | 3/1999 |
| WO | WO 2013/134597 | 9/2013 |

OTHER PUBLICATIONS

Written Opinion of the International Searching Authority (KIPO) for international application PCT/KR2014/010083 dated Nov. 27, 2014 with English translation.

Notice of Allowance from KIPO for Korean priority application 10-2013-0127240 dated Nov. 29, 2013 with English translation.

Partial supplementary European Search Report issued by the European Patent Office for corresponding European application 14856373.7 dated Mar. 22, 2017.

Extended European Search Report from European Patent Office issued for corresponding European application 14856373.7, dated Jul. 13, 2017.

\* cited by examiner

QUALITY ASSURANCE SYSTEM FOR RADIATION THERAPY EQUIPMENT, AND QUALITY ASSURANCE METHOD THEREOF

CROSS-REFERENCE TO RELATED APPLICATIONS

This application is the National Stage entry under 35 U.S.C. § 371 of International Application No. PCT/KR2014/010083 filed on Oct. 24, 2014, published on Apr. 30, 2015 under publication number WO 2015/060691 A1, which claims the benefit of priority under 35 U.S.C. § 119 of Korean Patent Application Number 10-2013-0127240 filed Oct. 24, 2013, which is incorporated herein by reference in its entirety.

TECHNICAL FIELD

The present inventive concept relates to a technology used for quality assurance of radiation therapy equipment, and more particularly, to a quality assurance system for radiation therapy equipment in which images for checking operation accuracy of radiation therapy equipment are obtained and then analyzed to determine the accuracy and control the quality of the radiation therapy equipment, and a quality assurance method thereof.

BACKGROUND ART

In radiation therapy using medical radiation therapy equipment, one of the most important factors is to focus radiation to a tumor while minimizing radiation to peripheral normal tissues. In particular, treatment techniques such as SBRT, SRS, IMRT, etc., which are recently introduced, require much higher precision and accuracy than existing 2D and 3D treatment techniques, due to a highly conformal dose distribution to a tumor with sharp dose fall off at the boundary.

Accordingly, quality assurance of the medical radiation therapy equipment has received much attention in the field of radiation therapy. The quality assurance of radiation therapy equipment globally follows recommendations made by the American Association Physics and Medicine (AAPM) of U.S. and the European Society for Radiotherapy and Oncology (ESTRO) of Europe. The quality assurance items in the recommendations are divided into two categories, one is a mechanical quality assurance, which verify the accuracy of geometry and mechanical components of the equipment and the other is radiation dose related quality assurance which assures the accuracy of the radiation from the equipment. The present invention related to the mechanical quality assurance.

The existing mechanical quality assurance methods of radiation therapy equipment use visual verification of the accuracy of three geometry centers which are, a gantry, a collimator, and a couch center while rotating each corresponding part. However, the method does not guarantee the measure in the degree of precision, that is less than 1 mm, required in the special treatments such as SBRT, SRS, IMRT, etc. In addition, the quality assurance results can be differing between measurers evaluating the radiation therapy equipment. In particular, aforementioned quality assurance methods are qualitative which are incapable of producing objective data, and thus, objectivity is very low and improvement is necessary.

Although Korean Patent No. 10-0981781 (Sep. 6, 2010) discloses a technology to improve performance of the existing radiation therapy equipment, there is a demand to develop technologies for an automatic evaluation system and method for quality assurance of radiation therapy equipment.

DETAILED DESCRIPTION OF THE INVENTIVE CONCEPT

Technical Problem

The present inventive concept provides a quality assurance system for radiation therapy equipment for assuring quality of radiation therapy equipment by capturing images of an indicating part of moving components of radiation therapy equipment and analyzing the captured images The present inventive concept provides an image processing unit to emphasize an edge of a region of a captured indicating part.

The present inventive concept further provides an image quality determination unit to determine whether an analyzed image quality is sufficient to determine the quality of radiation therapy equipment.

The present inventive concept provides a center point extraction unit to accurately determine an operation state of radiation therapy equipment.

The present inventive concept is to determine quality of radiation therapy equipment by measuring a movement range of coordinates of a center point.

The present inventive concept further provides data and information on the measured value required correction when radiation therapy equipment is in an abnormal state requiring correction or repair.

The quality assurance method for radiation therapy equipment using the present inventive concept provides a method in which, during operation of radiation therapy equipment, capturing images of indicating parts of moving components in operation of radiotherapy equipment indicating part and used to determine the quality of the radiation therapy equipment based on movement range of a center point in a region of the indicating parts.

Technical Solution

According to an aspect of the present inventive concept, one or more embodiments of the present inventive concept include a quality assurance system for radiation therapy equipment, which includes an image capturing unit installed on radiation therapy equipment and capturing images of an indicating parts indicating an operational state of the radiation therapy equipment, an image processing unit extracting an edge of the indicating part image captured by the image capturing unit, a center point extraction unit extracting a center point with respect to the edge, and a quality evaluation unit evaluating quality of the radiation therapy equipment by tracking movement of the center point.

The image processing unit may include an image binarization unit binarizing an original image of the indicating part by applying a critical value to the original image, and an edge emphasis unit extracting an edge of the indicating part from a binarized image generated by the image binarization unit.

The system, which is connected to a quality assurance control unit, may further include an image quality determination unit determining whether evaluation of quality is possible or not, based on a state of the edge extracted by the image processing unit, in which the state of the edge is determined based on a shape of the edge or a clearness of image owing to a difference between pixel brightness values of a shape and pixels included in a background area.

The quality evaluation unit may include a center point tracking unit tracking the coordinates of the center points of the consecutive frames of images extracted by the center point extraction unit, and a quality determination unit determining quality of the radiation therapy equipment based on whether a range of movement of the center points exceed a tolerance or not.

According to an aspect of the present inventive concept, there is provided a quality assurance method for radiation therapy equipment, which includes (a) obtaining original images for quality assurance of radiation therapy equipment by capturing images of an indicating part installed on the radiation therapy equipment, by using an image capturing unit, (b) extracting an edge of the indicating part by processing the original images, by using an image processing unit, (c) extracting a center point of the edge by using a center point extraction unit, and (d) evaluating quality of the radiation therapy equipment based on movement range of a center point by using a quality evaluation unit.

The operation (b) may include (b-1) setting a critical value for binarization, by using an image binarization unit, (b-2) binarizing the original image, by using the critical value, and (b-3) extracting an edge of an indicating part area from a binarized image, by using an edge emphasis unit.

The method may further includes, after the operation (b), (e) determining whether an image quality is good enough in which evaluation of machine quality is possible according to an emphasized shape or clearness of the edge by using an image quality determination unit.

The operation (e) may include (e-1) calculating a shape or clearness of the edge, and (e-2) determining whether clearness of the edge is equal to or less than a set value, in which, when the shape or clearness of the edge determined in the operation (e-2) is equal to or less than the set value, controlling a critical value of the image binarization unit is performed.

The operation (d) may include (d-1) tracking movement of a center point in each of consecutive frames of images by using a center point tracking unit, (d-2) determining whether a range of a movement of the center points is equal to or greater than a tolerance, by using a quality determination unit, (d-3) when the range of a movement of the center point determined in the operation (d-2) is less than the tolerance, determining that the radiation therapy equipment is in a normal state, and (d-4) when the range of a movement of the center point determined in the operation (d-2) is greater than the tolerance, determining that the radiation therapy equipment is in an abnormal state requiring correction or repair.

Advantageous Effects

In the quality assurance system for radiation therapy equipment according to the present inventive concept, by capturing images of indicating parts of moving components in operation of radiotherapy equipment and by analyzing the captured images, accuracy and reliability of the quality assurance of radiation therapy equipment can be greatly improved, and furthermore, precision of next generation radiation therapy, like particle beam therapy using protons, carbon, etc, is secured and the quality of radiation therapy may be greatly improved.

In the quality assurance method for radiation therapy equipment according to the present inventive concept, the quality of radiation therapy equipment can be accurately determined based on movement range of a center point of the indicating part obtained in images. Accordingly, when the radiation therapy equipment operates abnormally, maintenance and repair work can be initiated quickly.

BEST MODE

Hereinafter, a quality assurance system for radiation therapy equipment according to the present inventive concept, and a quality assurance method thereof, are described below in detail with reference to the accompanying drawings.

Figure 9:
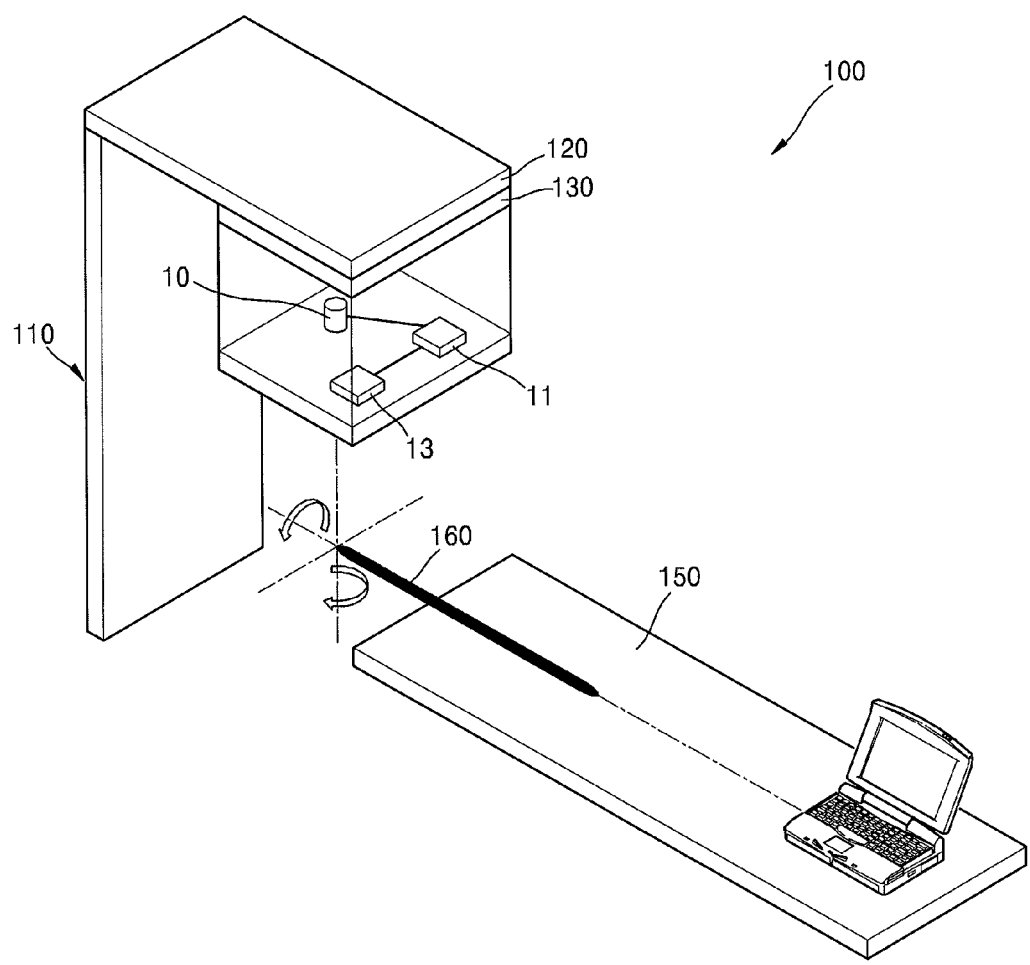
FIG. 9 is a perspective view of a quality assurance system for radiation therapy equipment according to an exemplary embodiment.

FIG. 9 is a perspective view of a quality assurance system 100 of radiation therapy equipment according to an exemplary embodiment.

Referring to FIG. 9, the quality assurance system 100 of radiation therapy equipment according to the present exemplary embodiment may include a main body portion 110, a gantry 120, a radiation emitting gantry head 130, a couch 150, and an indicating part 160. Also, the quality assurance system 100 of radiation therapy equipment may further include an image capturing unit 10, an angle sensor 11, and a signal collector 13.

A radiation therapy is a therapy to treat cancer by intensively deliver high-dose radiation to a tumor. For a successful radiation therapy, a therapy technique which can reduce damage to surrounding normal organs and simultaneously focus radiation to a tumor, precise radiation therapy equipment, and various types of imaging equipment is necessary. Recently, as high precision radiation therapy equipment is increasingly distributed, high-dose radiation therapy using highly complicated therapy technique is widely used. Although tumor eradication rate is improved through the high-dose radiation therapy a risk of potential radiation accidents due to wrong radiation—increases as well. Accordingly, strict quality assurance of therapy equipment for prevention of occurrence of such an accident is regulated by laws.

The main body portion 110 forms a base portion of the radiation therapy equipment, and becomes a basis of rotation of the gantry 120, the radiation emitting gantry head 130, an image acquisition unit 140, and the couch 150.

The gantry 120 may be coupled to one side of the main body portion 110 to be capable of rotating in at least one direction with respect to the main body portion 110. In this state, the image capturing unit 10 formed at one side of the gantry 120 and the radiation emitting gantry head 130 may rotate with the gantry 120. In other words, the gantry 120, the radiation emitting gantry head 130, and the image capturing unit 10 may be capable of rotating in a direction indicated by an arrow of FIG. 9 or in a reverse direction thereof.

The radiation emitting gantry head 130 for emitting radiation is formed at one side of the gantry 120. The radiation emitting gantry head 130 may emit an X-ray, a gamma ray, high energy electrons, high energy protons, or high energy particles.

Also, the radiation emitting gantry head 130 may include any one of an X-ray generation apparatus, a radioactive isotope source, and a linear accelerator. Alternatively, the radiation emitting gantry head 130 may receive and emit a high energy particle beam generated by being accelerated in a particle accelerator. Also, the radiation emitting gantry head 130 may be equipped with a multi-leaf collimator (MLC). Since the radiation emitting gantry head 130 can shaping a beam by using the MLC, transfer of radiation energy may be performed more efficiently.

The couch 150 which is made a patient lies thereon, and may be configured to move in an X-axis direction, a Y-axis direction, and a Z-axis direction with respect to the radiation emitted from the radiation emitting gantry head 130.

The indicating part 160 is formed to have a predetermined tip shape, is installed on the couch 150, and performs a function to indicate an isocenter point of the radiation therapy equipment. The image capturing unit 10 continuously captures images of the indicating part 160 and thus checks whether the radiation emitting gantry head 130 accurately rotates around the isocenter point.

Alternatively, the image capturing unit 10, the angle sensor 11, and the signal collector 13 may be arranged at one side of the radiation emitting gantry head 130.

The image capturing unit 10 captures an image generated based on the motion of the radiation emitting gantry head 130, and the angle sensor 11 may measure rotation angles of the gantry 120, the radiation emitting gantry head 130, and the couch 150. The image capturing unit 10 may include a wired or wireless camera. The center point of the radiation emitting gantry head 130 may be detected by using the image capturing unit 10 and the angle sensor 11. In this stage, the image capturing unit 10 and the angle sensor 11 continuously detect the center point of the radiation emitting gantry head 130 while the gantry 120, the radiation emitting gantry head 130, or the couch 150 rotates. Accordingly, quality assurance of the radiation therapy equipment such as a degree of accuracy of the isocenter point, a degree of accuracy of the size of an light field, and a degree of accuracy of the position of an MLC leaf of the radiation therapy equipment can be performed.

Although FIG. 9 illustrates that the image capturing unit 10 and the angle sensor 11 are arranged at one side of the radiation emitting gantry head 130 and rotate together with the radiation emitting gantry head 130 so as to detect the center point by capturing images of the indicating part 160, the technical concept of the present inventive concept is not limited thereto. In other words, the image capturing unit 10 and the angle sensor 11 can be attached on the couch 150 and rotate together with the couch 150 so as to capture an image of the indicating part 160, thereby detecting the center point of the radiation emitting gantry head 130.

Figure 1:
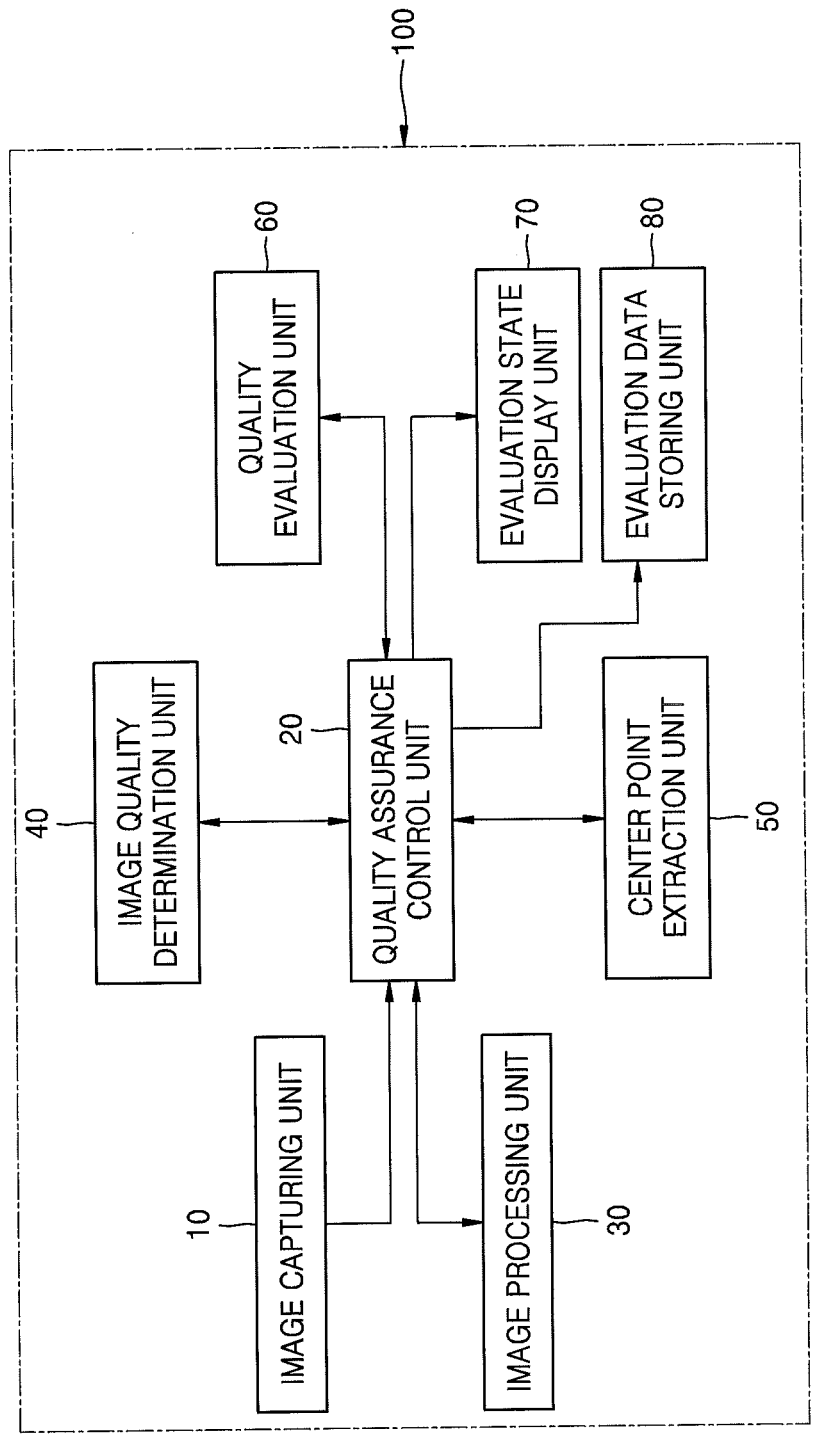
FIG. 1 is a block diagram illustrating an overall structure of a quality assurance system for radiation therapy equipment according to the present inventive concept.

A signal obtained by the image capturing unit 10 and the angle sensor 11 may be collected by the signal collector 13 and signal processing may be performed at each element of FIG. 1 by using the collected data.

FIG. 1 is a block diagram illustrating an overall structure of the quality assurance system 100 of radiation therapy equipment according to the present inventive concept. The quality assurance system 100 of radiation therapy equipment according to the present inventive concept may include the image capturing unit 10, a quality assurance control unit 20, an image processing unit 30, an image quality determination unit 40, a center point extraction unit 50, a quality evaluation unit 60, an evaluation state display unit 70, and an evaluation data storing unit 80.

The image capturing unit 10 is installed on the radiation therapy equipment and captures images of an indicating part (see 160 of FIG. 9) indicating an operation state of the radiation therapy equipment. The image capturing unit 10 may perform a function of capturing an image of the indicating part installed on the radiation therapy equipment at a position corresponding to a gantry (see 120 of FIG. 9).

The quality assurance control unit 20 is connected to the image capturing unit 10 and analyzes the captured image of the indicating part, thereby controlling a determination of quality of the radiation therapy equipment.

Figure 2:
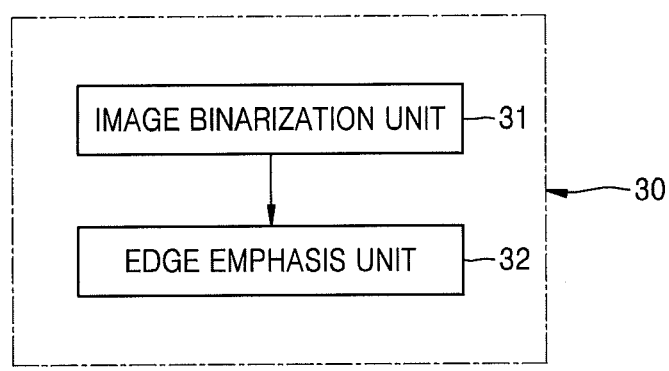
FIG. 2 is a block diagram illustrating a detailed structure of an image processing unit, in the quality assurance system for radiation therapy equipment according to the present inventive concept.

The image processing unit 30 extracts an edge of the indicating part image captured by the image capturing unit according to a control signal from the quality assurance control unit 20. The image processing unit 30 according to the present inventive concept may include an image binarization unit 31 and an edge emphasis unit 32, as illustrated in FIG. 2.

Figure 3:
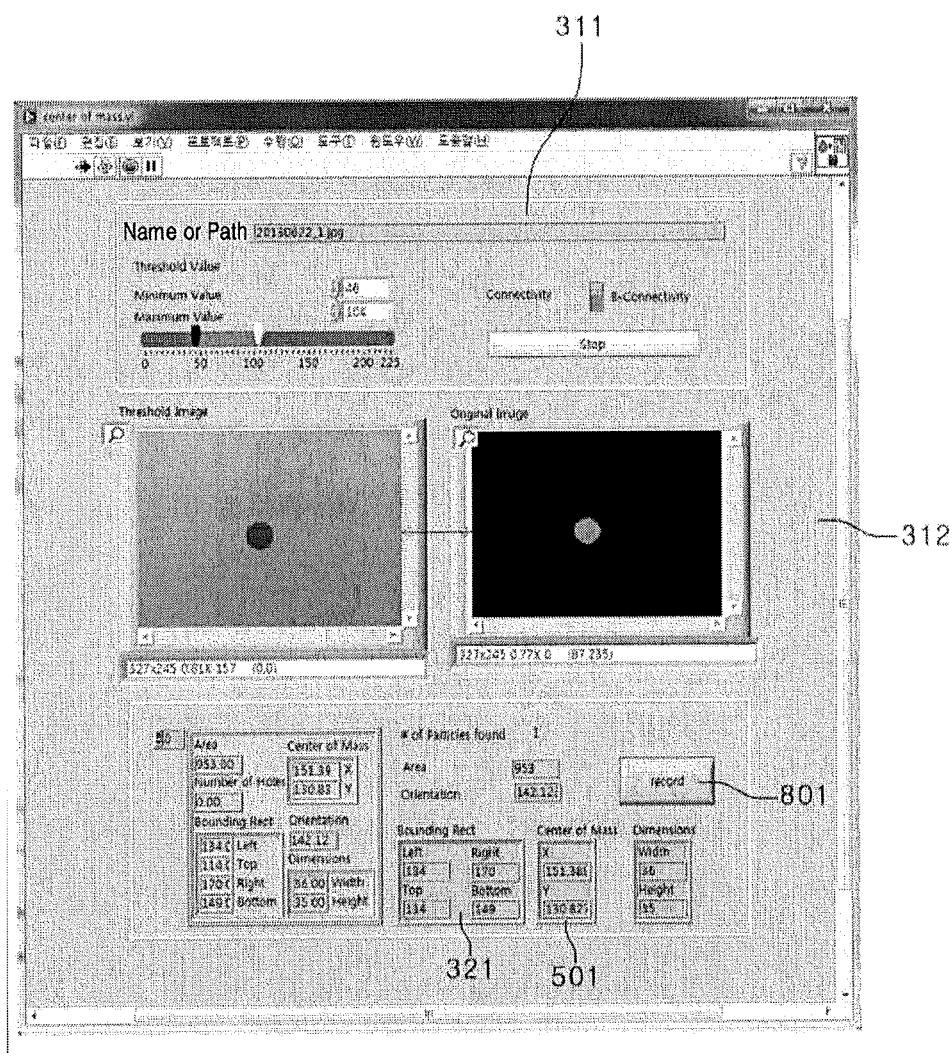
FIG. 3 is an image showing an exemplary embodiment of an evaluation state display unit, in the quality assurance system for radiation therapy equipment according to the present inventive concept.

The image binarization unit 31, as shown in an exemplary embodiment illustrated in FIG. 3, binarizes the captured original image of the indicating part by applying a critical value to the captured original image. The edge emphasis unit 32 extracts an edge of the indicating part from a binary image generated by the image binarization unit 31 using a high pass filter.

The image quality determination unit 40 is connected to the quality assurance control unit 20 and determines whether quality evaluation is possible or not with an edge images generated as a result of the image processing of the image processing unit 30. The state of an edge according to the present inventive concept may be determined by the shape of an edge or a clearness of image owing to a difference in a pixel brightness value from a background area. When the edge of the image processed by the image processing unit 30 does not suitable for the determination of quality, an edge may be extracted again by adjusting the critical value in the image binarization unit 31.

Accuracy in a quality assurance of the radiation therapy equipment can be improved by the image quality determination unit 40 according to the present inventive concept.

The center point extraction unit 50 extracts a center point based on the edge extracted by the image processing unit 30. In the present inventive concept, the center point extraction unit 50 may calculate coordinates of a center point of an edge area of each of consecutive frames of images to check a movement range of the center point due to the rotation of the radiation therapy equipment.

Figure 4:
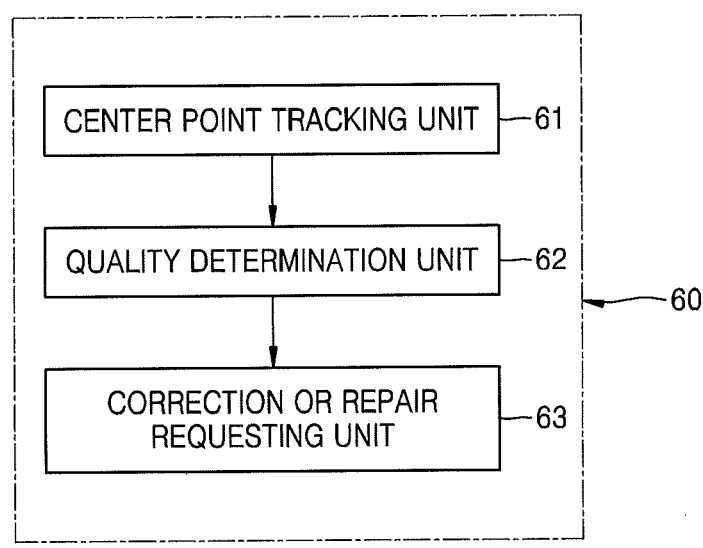
FIG. 4 is a block diagram illustrating a detailed structure of a quality evaluation unit, in the quality assurance system for radiation therapy equipment according to the present inventive concept.

The quality evaluation unit 60 performs a function to evaluate the quality of the radiation therapy equipment by tracking a movement of the center point. The quality evaluation unit 60 according to the present inventive concept may include a center point tracking unit 61, a quality determination unit 62, and a correction or repair requesting unit 63, as illustrated in FIG. 4.

The center point tracking unit 61 according to the present inventive concept tracks coordinates of a center point of each of the consecutive frames of images extracted by the center point extraction unit 50. The quality determination unit 62 determines the quality of the radiation therapy equipment based on whether a movement range of the coordinates of the center point exceeds a tolerance. The correction or repair requesting unit 63 is connected to the quality determination unit 60 and generates information about a measured value required correction or a repair request when the radiation therapy equipment is determined to be in an abnormal state that requires correction or repair.

The operation state of the radiation therapy equipment may be accurately determined by using the quality evaluation unit 60. As a quality is determined based on a standard, reliability and accuracy of the quality assurance may be secured.

The evaluation state display unit 70 is connected to the quality assurance control unit 20 and displays at least one of an original image for evaluation of quality, a processed image varying according to image processing results, edge information, and the coordinates of a center point.

In the present exemplary embodiment, the evaluation state display unit 70 is implemented as illustrated in FIG. 3, and may include a critical value control unit 311 receiving inputs of information about a path of an obtained image and a signal for setting and controlling a critical value of the image binarization unit 31, an image display unit 312 displaying an analyzed image, edge information 321, input button 801 storing center point coordinate information 501 and a quality assurance work information. A quality assurance results of the radiation therapy equipment may be obtained in real time through the evaluation state display unit 70.

The evaluation data storing unit 80 is connected to the quality assurance control unit 20 and stores quality evaluation information of the radiation therapy equipment. The evaluation data storing unit 80 according to the present inventive concept may include a date, a name of measurer, image information, and tolerance for quality assurance of the radiation therapy equipment.

As described above, when the quality assurance system for radiation therapy equipment according to the present inventive concept is used, accuracy and reliability of the quality assurance of the radiation therapy equipment can be greatly improved by capturing an image of the indicating part indicating the operation of the radiation therapy equipment and analyzing the captured images.

Figure 5:
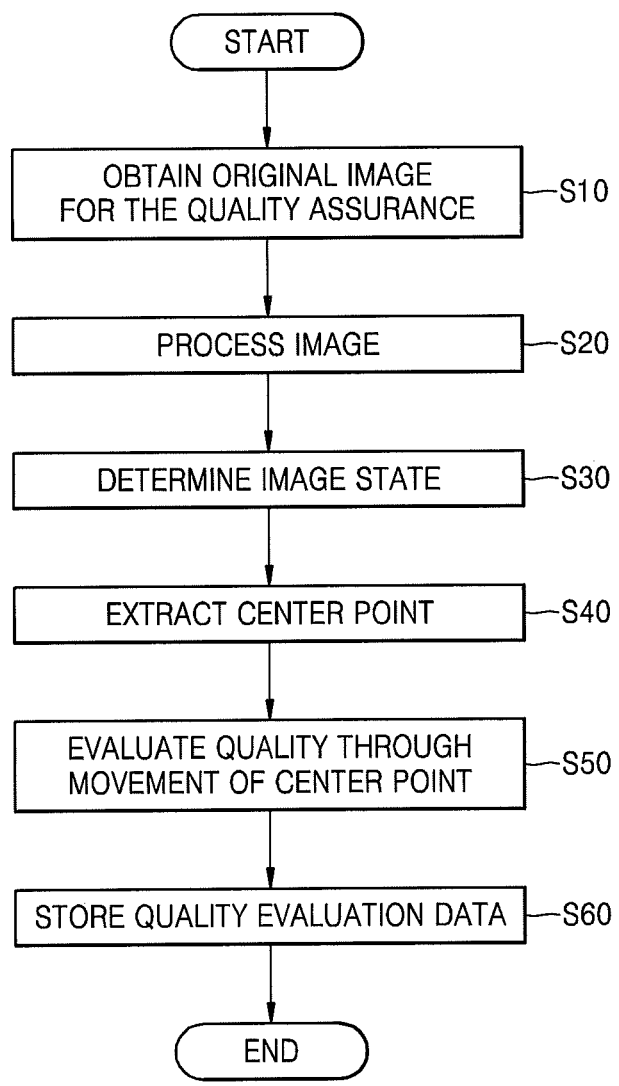
FIG. 5 is a flowchart for explaining an overall flow of a quality assurance method for radiation therapy equipment according to the present inventive concept.

FIG. 5 is a flowchart for explaining an overall flow of a quality assurance process for radiation therapy equipment according to the present inventive concept. The indicating part installed on the radiation therapy equipment is captured by using the image capturing unit 10, and thus, an original image for the quality assurance of radiation therapy equipment is obtained (S10). In the operation S10, a state of the indicating part indicating the rotation of the gantry or a collimator of the radiation therapy equipment is captured as a video and thus a video is obtained.

Figure 6:
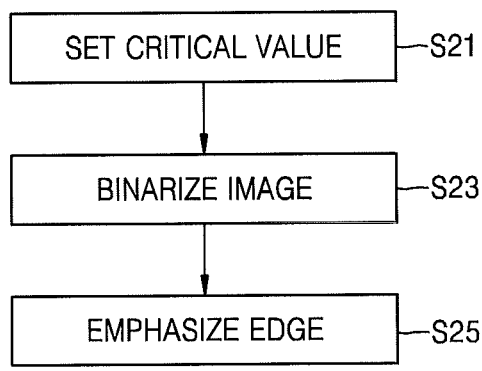
FIG. 6 is a flowchart for explaining a detailed flow of Operation S20, in the quality assurance method for radiation therapy equipment according to the present inventive concept.

Next, an edge of the shape of an indicating part is extracted by using the image processing unit 30 processing the original image (S20). The operation S20 according to the present inventive concept includes, as illustrated in FIG. 6, setting a critical value in the image binarization unit 31 (S21) for binarization, binarizing the original image by using the critical value (S23), and extracting the edge area of the indicating part from a binarized image by using the edge emphasis unit 32 (S25). In the present exemplary embodiment, in the operation S25, the edge area of the indicating part is extracted by using a high pass filter.

Figure 7:
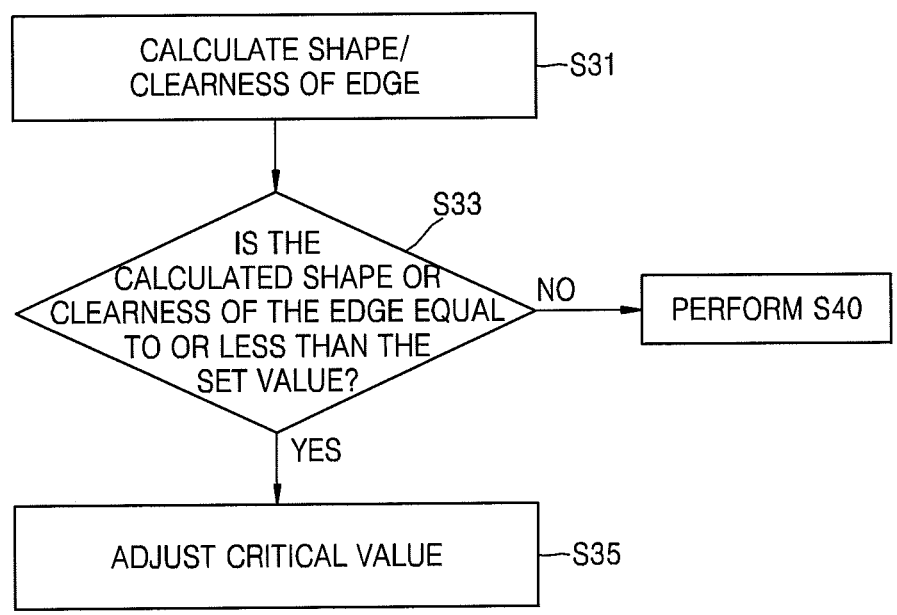
FIG. 7 is a flowchart for explaining a detailed flow of Operation S30, in the quality assurance method for radiation therapy equipment according to the present inventive concept.

Next, whether an image quality is high enough to be used for the evaluation of machine quality is determined based on the emphasized shape or clearness of the edge shape by using the image quality determination unit 40 (S30). The operation S30 according to the present inventive concept includes, as illustrated in FIG. 7, calculating the shape or clearness of the edge shape and (S31) and determining whether the calculated shape or clearness of the edge shape is equal to or less than the set value (S33).

When the shape or clearness of the edge shape is determined in the operation S33 to be equal to or less than the set value, the critical value of the image binarization unit 31 is adjusted (S35).

Unnecessary quality assurance process may not be performed through the operation S30 and thus optimal images for quality assurance may be provided.

Next, a center point of the edge is extracted by using the center point extraction unit 50 (S40).

Figure 8:
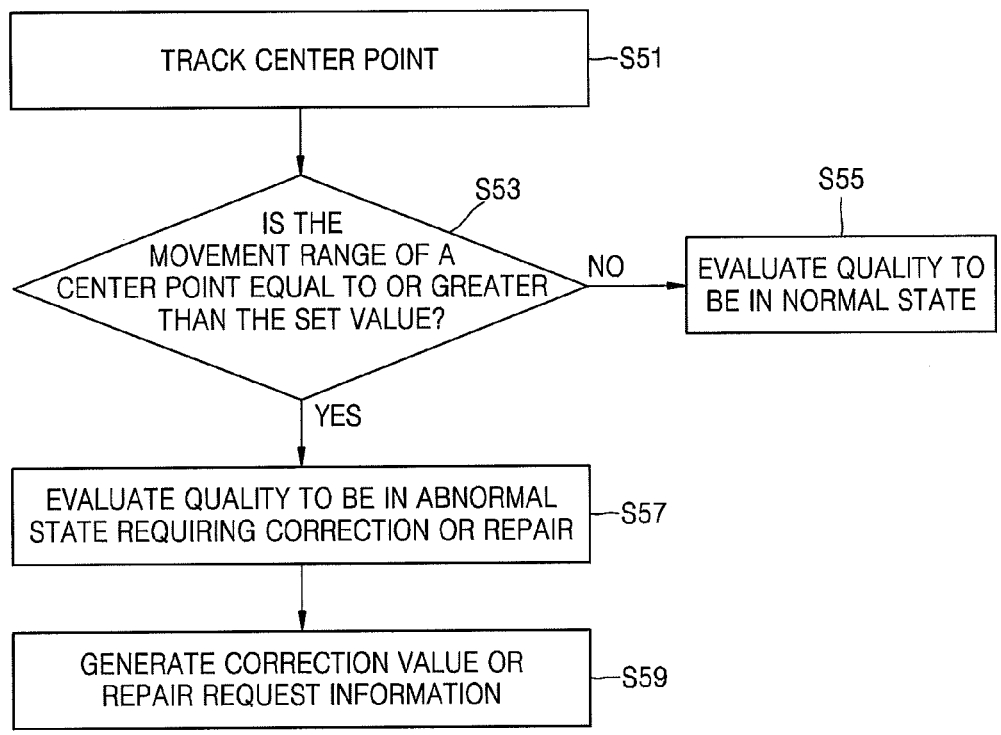
FIG. 8 is a flowchart for explaining a detailed flow of Operation S50, in the quality assurance method for radiation therapy equipment according to the present inventive concept.

Next, the quality of radiation therapy equipment is evaluated based on a movement range of a center point by using the quality evaluation unit 60 (S50). In the operation S50 according to the present inventive concept, as illustrated in FIG. 8, the movement of the center point in each of the consecutive frames of images is tracked by using the center point tracking unit 61 (S51). In the present inventive concept, in the operation S51, the movement of the center point may be tracked by doing a pattern matching with a reference shape set previously.

Next, whether a movement range of the center point is equal to or greater than a tolerance is determined by using the quality determination unit 62 (S53). In the present inventive concept, in addition to the movement of the center point in the operation S53, a change in the absolute size of the edge area and the relative size of the edge in an entire image may be taken into consideration.

When the movement range of the center point is determined to be less than the tolerance in the operation S53, the quality of radiation therapy equipment is determined to be in a normal state (S55). When the movement range of the center point is determined to be equal to or greater than the tolerance in the operation S53, the quality of radiation therapy equipment is determined to be in an abnormal state which requires correction or repair (S57). A measured value requires correction or repair requesting information is generated by using the correction or repair requesting unit 53 (S59).

Next, information about the quality assurance work of radiation therapy equipment is stored by using the evaluation data storing unit 80 (S60). In the operation S60 according to the present inventive concept, information about any one or more of a date, an name of measurer, image, and a tolerance (internationally recommended values) for quality assurance determination of the radiation therapy equipment is stored. Through the operation S60, information and results about the quality assurance of radiation therapy equipment may be systematically managed.

As described above, when the quality assurance method for radiation therapy equipment invented by the presented concept is used, the quality of radiation therapy equipment operation may be accurately determined by examining the movement range of a center point of the indicating part that is obtained as an image. When the radiation therapy equipment is in abnormal operation, a maintenance and repair work can be quickly requested. Furthermore, precision of a next generation radiation therapy such as particle beam therapy using protons or carbon, etc is secured and the quality of radiation therapy may be greatly improved.

While one or more exemplary embodiments have been described with reference to the figures, various quality assurance systems of radiation therapy equipment and various quality assurance methods thereof may be implemented without departing from the spirit and scope of the present inventive concept.

FIG. 3 shows an image for checking accuracy of an isocenter point of radiation therapy equipment by using the quality assurance system for radiation therapy equipment according to the present inventive concept. In other words, while the gantry, the radiation emitting gantry head 130, or the couch 150 rotates, the indicating part is continuously captured and the center point of the radiation emitting gantry head 130 is detected by using the captured images. Accordingly, whether the isocenter point is confined within a predetermined range, for example, within ±1 mm, or not can be tested. As such, in the quality assurance system for radiation therapy equipment according to the present inventive concept, accuracy test of the isocenter point of the radiation therapy equipment can be automatically performed without manual interruption.

Mode of the Inventive Concept

In the following description, a quality assurance system for radiation therapy equipment according to another exemplary embodiment is discussed.

Figure 10:
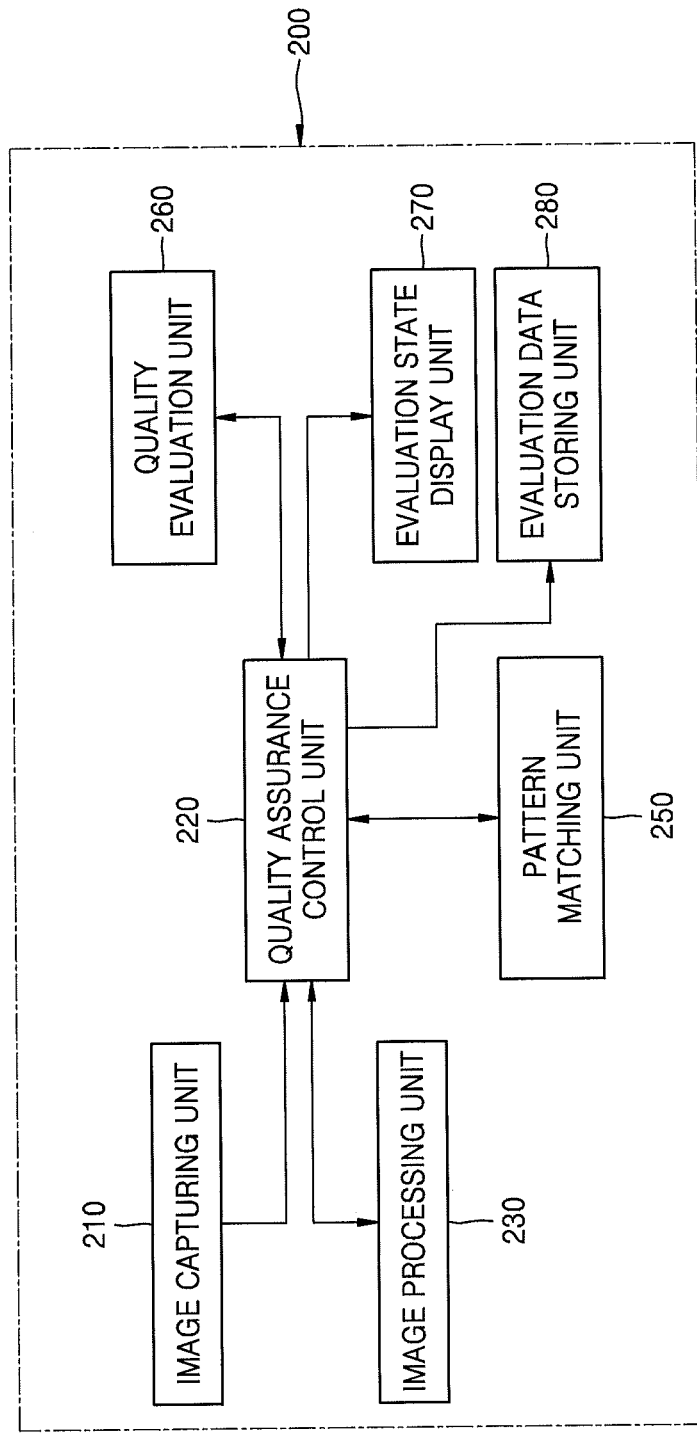
FIG. 10 is a block diagram illustrating an overall structure of a quality assurance system for radiation therapy equipment according to another exemplary embodiment.

FIG. 10 is a block diagram illustrating an overall structure of a quality assurance system for radiation therapy equipment according to another exemplary embodiment. FIGS. 11A to 11D are images showing performing quality assurance by a quality assurance system for radiation therapy equipment according to another exemplary embodiment.

Referring to FIG. 10, a quality assurance system 200 of radiation therapy equipment according to another exemplary embodiment may include an image capturing unit 210, a quality assurance control unit 220, an image processing unit 230, a pattern matching unit 250, a quality evaluation unit 260, an evaluation state display unit 270, and an evaluation data storing unit 280.

The image capturing unit 210 is installed on the radiation therapy equipment and captures images of an indicating part r (see 160 of FIG. 9) that indicates an operation state of the radiation therapy equipment. The image capturing unit 210 captures an image of the indicating part installed on the radiation therapy equipment at a position corresponding to the radiation emitting gantry head of the radiation therapy equipment.

The quality assurance control unit 220 is connected to the image capturing unit 210 and controls an operation of determining a quality state of radiation therapy equipment by analyzing the image captured by the indicating part.

The pattern matching unit 250 extracts a center point of the image by using pattern matching, and a change of the center point, from the image obtained by the image capturing unit 210 according to a control signal of the quality assurance control unit 220.

In the quality assurance system 200 of radiation therapy equipment according to the present exemplary embodiment, other elements are the same as those of the quality assurance system 100 of radiation therapy equipment of FIG. 1 and characteristically differ only in the algorithm of extracting a center point, which is discussed in detail in the following description.

In detail, in the extracting of the center point in the quality assurance system 100 of radiation therapy equipment described in FIG. 1, an edge is extracted and a center point is extracted therefrom. In contrast, in the quality assurance system 200 of radiation therapy equipment of FIG. 1, a center point of the image is extracted by using to pattern matching.

The pattern matching signifies a method of collecting information by classifying a predetermined image by pixels and searching for an area having information most similar to the predetermined image from a newly captured image.

Figure 11A:
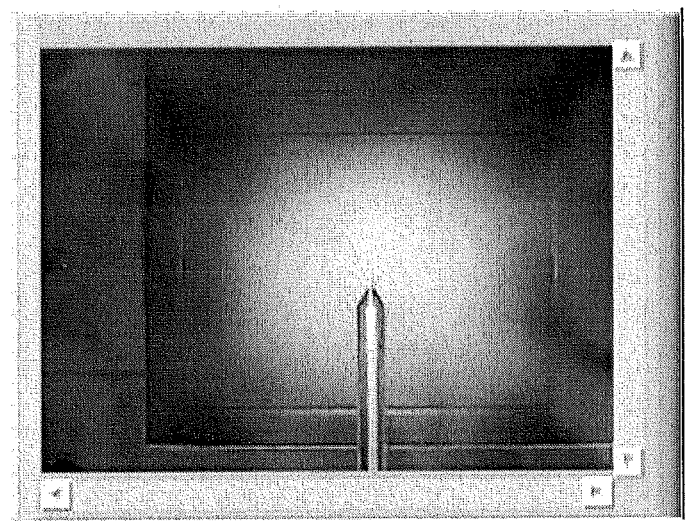
FIGS. 11A to 11D are images showing operations of performing quality assurance by using a quality assurance system for radiation therapy equipment according to another exemplary embodiment.
Figure 11B:
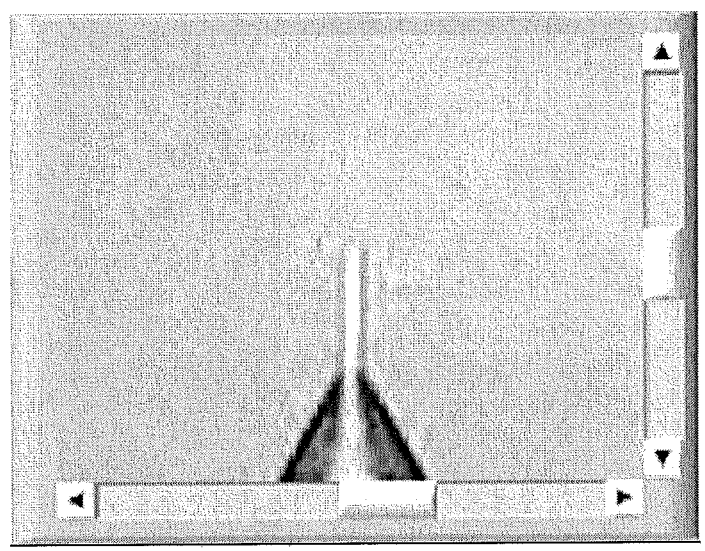

In detail, FIG. 11A is an image showing an the indicating part (see 160 of FIG. 9) indicating an isocenter point of the radiation therapy equipment which is captured by the image capturing unit 210. FIG. 11B shows an image of a preset indicating part (see 160 of FIG. 9).

Figure 11C:
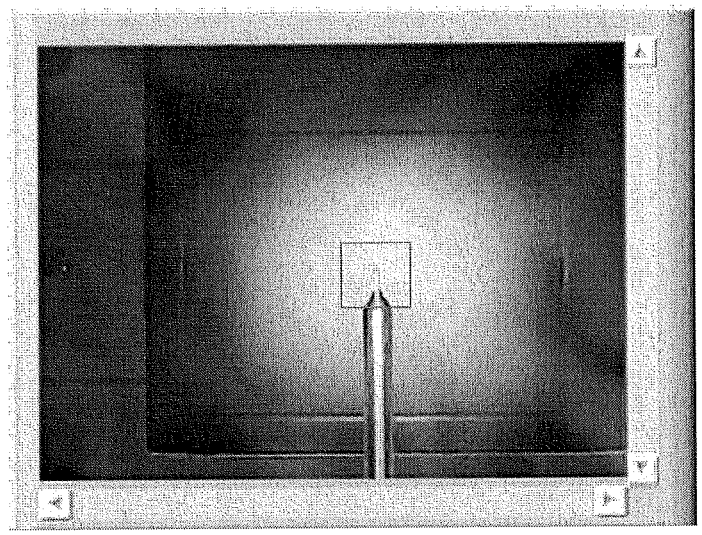
Figure 11D:
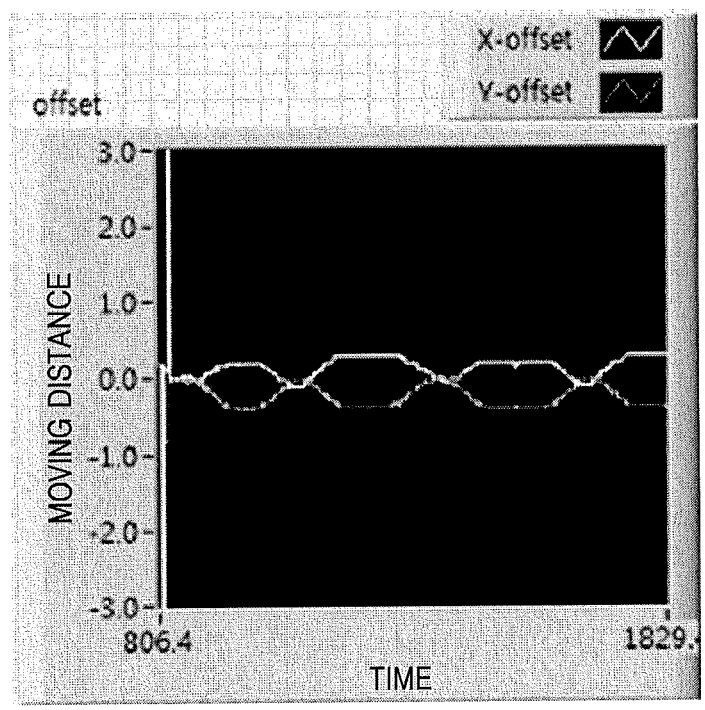

The pattern matching unit 250 detects an area having a pattern that is most similar to the indicating part (see 160 of FIG. 9) shown in FIG. 11B, in an image obtained in real time by the image capturing unit 210, that is, the image of FIG. 11A, and tracking and storing an area having a pattern that is most similar to the indicating part (see 160 of FIG. 9) as shown in FIG. 11C. A change of the center point of radiation is measured by assessing the movement of the indicating part while tracking the indicating part. FIG. 11D shows a change of the center point measured as described above.

The quality evaluation unit 260 tracks a movement of the center point and evaluates quality of the radiation therapy equipment. The quality evaluation unit 60 according to the present exemplary embodiment may include a center point tracking unit (see 61 of FIG. 4), a quality determination unit (see 62 of FIG. 4), and a correction or repair requesting unit (see 63 of FIG. 4).

The evaluation state display unit 270 is connected to the quality assurance control unit 220 and displays at least one of an original image for quality evaluation, a processed image varying according to image processing, pattern information, and coordinates of a center point.

The evaluation data storing unit 280 is connected to the quality assurance control unit 220 and stores quality evaluation information of radiation therapy equipment. The evaluation data storing unit 280 according to the present exemplary embodiment may include a date, a name of measurer, image information, and information about tolerance for quality assurance determination of the radiation therapy equipment.

As described above, when the quality assurance system for radiation therapy equipment according to the present exemplary embodiment is used, accuracy and reliability of the quality assurance of radiation therapy equipment can be greatly improved by capturing an image of the indicting part indicating the operation of radiation therapy equipment and analyzing the captured images.

Figure 12:
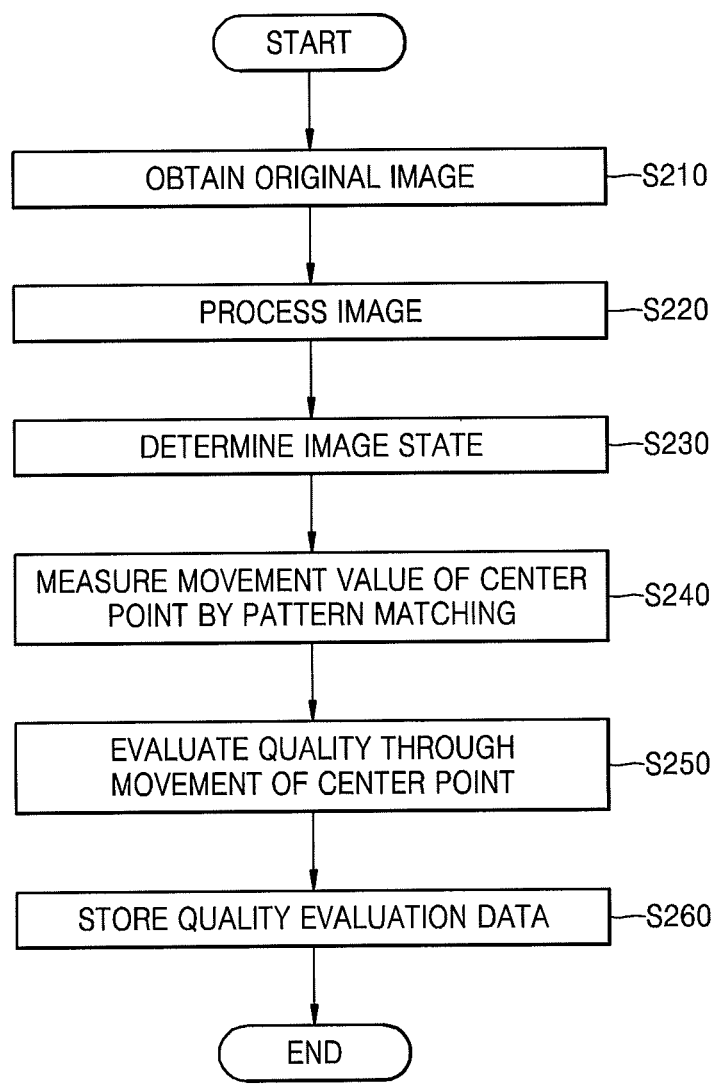
FIG. 12 is a flowchart for explaining a detailed flow of a quality assurance method for radiation therapy equipment according to another exemplary embodiment.

FIG. 12 is a flowchart for explaining a detailed flow of a quality assurance method for radiation therapy equipment according to another exemplary embodiment. Referring to FIG. 12, the quality assurance method for radiation therapy equipment according to another exemplary embodiment is described as follows.

First, the indicating part installed on the radiation therapy equipment is captured by using the image capturing unit 210, and thus, an original image for the quality assurance of radiation therapy equipment is obtained (S210). In the operation S210, a state of the indicating part indicating the rotation of the gantry or the radiation emission part of the radiation therapy equipment is captured as a video and thus the video is obtained.

Next, the original image is processed by using the image processing unit 230 (S220). Whether the quality of the processed image is high enough to be used is evaluated (S230).

Next, a center point of an image obtained by using pattern matching, and a change of the center point, are extracted by the pattern matching unit 250 from the image obtained by the image capturing unit 210 (S240). The pattern matching signifies a method of collecting information by classifying a predetermined image by pixels and searching for an area having information most similar to the predetermined image from a newly captured image.

The pattern matching unit 250 detects an area having a pattern that is most similar to the indicating part (see 160 of FIG. 9) shown in FIG. 11B, in an image obtained in real time by the image capturing unit 210, that is, the image of FIG. 11A, and tracking and storing an area having a pattern that is most similar to the indicating part (see 160 of FIG. 9) as shown in FIG. 11C. A change of the center point is measured by assessing the movement of the indicating part while tracking the indicating part.

Next, the quality of radiation therapy equipment is evaluated with a movement range of the center point by using the quality evaluation unit 260 (S250).

Next, information about the quality assurance work of radiation therapy equipment is stored by using the evaluation data storing unit 280 (S260). In the operation S260 according to the present inventive concept, information about any one or more of a date, a name of measurer, image information, and a tolerance (internationally recommended value) for quality assessment of the radiation therapy equipment is stored. Through the operation S260, data and information about the quality assurance of radiation therapy equipment may be systematically managed.

As described above, when the quality assurance method for radiation therapy equipment according to the present exemplary embodiment is used, accuracy and reliability of the quality assurance of radiation therapy equipment can be greatly improved by capturing an image of the indicting member indicating the operation of radiation therapy equipment and analyzing the captured images.

Next, a process of checking the light field size of the radiation therapy equipment by using the quality assurance system for radiation therapy equipment according to the present inventive concept is described.

Figure 13A:
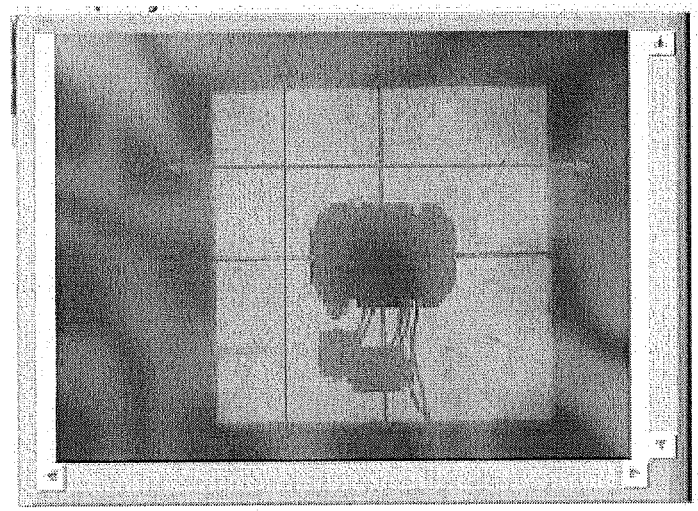
FIGS. 13A to 13C are images for checking accuracy of a size of a light field of radiation therapy equipment, which are determined by the quality assurance system for radiation therapy equipment according to an exemplary embodiment.
Figure 13B:
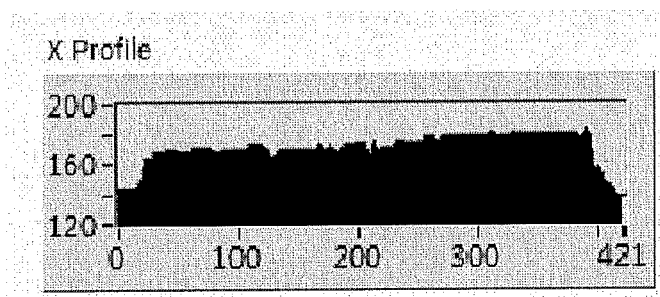
Figure 13C:
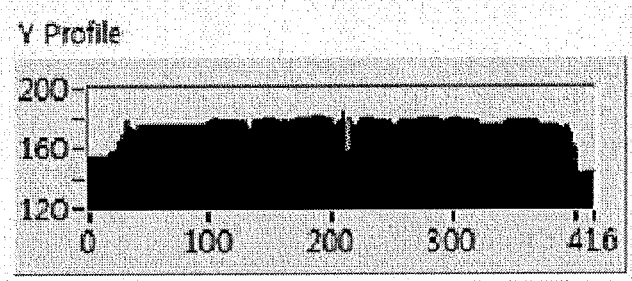

FIGS. 13A to 13C are images checking accuracy of a light field size of radiation therapy equipment, by using the quality assurance system for radiation therapy equipment according to an exemplary embodiment.

As illustrated in FIG. 13A, the image capturing unit 10 captures an image of the light field size projected onto the couch 150 and initiates signal processing by transferring a captured image to the image processing unit 230 via the signal collector 13. In this case, although not illustrated in the drawings, a unit determining the accuracy of the light field size (not shown) may be further provided. The light field accuracy determination unit may calculate a full width at half maximum (FWHM) with respect to a light field image and determine the calculated FWHM as a light field width. In other words, pixel values selected in X-axis and Y-axis directions are obtained in an image obtained by the image capturing unit 10 and thus the size of a light field may be determined by calculating the FWHM in the X-axis and the Y-axis. FIG. 13B shows an obtained pixel values along the selected X-axis and a FWHM value calculated using the obtained pixel values. FIG. 13C shows an obtained pixel values along the selected Y-axis and a FWHM value calculated using the obtained pixel values.

Although, in the above description, capturing images of a rotation center while the gantry or light field rotates, a rotation center thereof is described in the quality assurance system for radiation therapy equipment according to the present inventive concept. However a movement of the couch center may be measured by using the same method described above. In other words, the position of the indicating part is tracked by using the pattern matching in the image obtained by the image capturing unit, and the movement of the couch in each of the X-axis, Y-axis, and Z-axis directions may be measured.

According to the present inventive concept, an automation of quality assurance system may be established. Also, as the automation of quality assurance is realized, a time taking for quality assurance work may be reduced much. Also, as quality assurance can be performed in weekdays, for example, a night time when patients treatment is finished or lunch time, due to a reduced time for measurement, the required number of quality assurance measurers and workload of radiation therapy equipment may be reduced. Furthermore, as a result of each item of quality assurance that has been performed is analyzed automatically and a quality assurance report is automatically generated and stored, history of quality assurance may be systematically analyzed and saved

INDUSTRIAL APPLICABILITY

The present inventive concept may be used for a quality assurance system for radiation therapy equipment and a quality assurance method thereof, in which an image for checking an operation state of radiation therapy equipment is obtained and then a quality state of radiation therapy equipment may be checked and controlled through an analysis work.

The invention claimed is:

1. A quality assurance system for radiation therapy equipment, the system comprising:

a main body portion;

a gantry coupled to one side of the main body portion and capable of rotating in at least one direction with respect to the main body portion;

a radiation emitting gantry head formed at one side of the gantry and emitting radiation;

a couch arranged at one side of the main body portion and capable of moving in at least one direction with respect to the main body portion;

an image capturing unit arranged adjacent to at least one of the gantry, and the radiation emitting gantry head and capturing at least one image generated based on the light exposed from the radiation emitting gantry head;

an image center point tracking device configured to perform pattern matching on the captured image, wherein the pattern matching comprises extracting a center point of each captured image and determining a position change of the center point;

an image analyzing device configured to evaluate quality of the radiation therapy equipment based on tracking movement of the center point; and an indicating part indicating a mechanical isocenter point of the radiation therapy equipment;

wherein the image capturing unit captures images of the indicating part.

2. The system of claim 1, wherein the image capturing unit continuously captures an image based on light that is exposed from the radiation emitting gantry head while at least one of the gantry, the radiation emitting gantry head, and the couch rotates, and the image center point tracking device extracts a center point of the light with respect to each of consecutive frames of images.

3. The system of claim 1, further comprising a light field accuracy determination unit that determines a degree of accuracy regarding a size of an light field by analyzing the captured image.

4. The system of claim 3, wherein the light field accuracy determination unit calculates a full width at half maximum (FWHM) with respect to a captured light field image and sets the calculated FWHM as an light field width.

5. The system of claim 1, wherein the indicating part is installed on the couch, and the image center point tracking device extracts, an area having a pattern that is most similar to the predefined pattern of the indicating part from the captured image.

6. The system of claim 1, wherein the image analyzing device calculates a size of a rotation center of a light field of the radiation emitting gantry head by analyzing the captured image and determines a degree of accuracy of the rotation center.

7. The system of claim 1, wherein the image center point tracking device determines a degree of accuracy of movement of the couch based on the captured image.

* * * * *